(12) United States Patent
Moll

(10) Patent No.: US 6,979,306 B2
(45) Date of Patent: Dec. 27, 2005

(54) METHOD AND DEVICE FOR MONITORING LOSS OF BODY FLUID AND DISLODGMENT OF MEDICAL INSTRUMENT FROM BODY

(75) Inventor: Bradley Jon Moll, Hot Springs, AR (US)

(73) Assignee: Moll Family Trust, San Diego, CA (US)

( * ) Notice: Subject to any disclaimer, the term of this patent is extended or adjusted under 35 U.S.C. 154(b) by 309 days.

(21) Appl. No.: 10/640,371

(22) Filed: Aug. 13, 2003

(65) Prior Publication Data

US 2005/0038325 A1 Feb. 17, 2005

(51) Int. Cl.$^7$ ............................ A61M 5/00; A61B 5/00; B01D 61/00; C02F 1/00
(52) U.S. Cl. .................. 604/4.01; 604/6.16; 604/5.01; 210/646; 210/739; 600/362; 600/371
(58) Field of Search ..................... 604/4.01, 5.01–5.04, 604/6.08, 6.09, 6.1, 6.11, 6.16; 210/600, 210/634, 645–646, 649–651, 739–741, 744–45, 210/767, 194, 195.1, 195.2, 252, 257.1, 572.2

(56) References Cited

U.S. PATENT DOCUMENTS

| | | | |
|---|---|---|---|
| 3,618,602 A | 11/1971 | Shaw | 128/214 |
| 3,631,437 A | 12/1971 | Campbell et al. | 340/239 |
| 3,864,676 A | 2/1975 | Macias et al. | 340/235 |
| 4,010,749 A | 3/1977 | Shaw | 128/214 |
| 4,083,777 A | 4/1978 | Hutchisson | 210/22 |
| 4,666,434 A | 5/1987 | Kaufman | 604/179 |
| 4,804,054 A | 2/1989 | Howson et al. | 128/898 |
| 4,846,807 A | 7/1989 | Safadago | 604/179 |
| 4,877,034 A | 10/1989 | Atkins et al. | 128/664 |
| 5,383,893 A | 1/1995 | Daneshvar | 606/201 |
| 5,779,657 A | 7/1998 | Daneshvar | 602/60 |
| 6,254,586 B1 | 7/2001 | Mann et al. | 604/506 |
| 6,461,329 B1 | 10/2002 | Van Antwerp et al. | 604/111 |
| 2002/0198483 A1 * | 12/2002 | Wariar et al. | 604/5.01 |
| 2003/0009131 A1 | 1/2003 | Van Antwerp et al. | 604/111 |

FOREIGN PATENT DOCUMENTS

| | | |
|---|---|---|
| DE | 197 34 002 C1 | 9/1998 |
| WO | WO 99/24145 | 5/1999 |

* cited by examiner

*Primary Examiner*—Patricia Bianco
(74) *Attorney, Agent, or Firm*—Stephen C. Beuerle; Procopio Cory Hargreaves & Savitch LLP

(57) ABSTRACT

A method of alerting medical personnel of a problem during hemodialysis includes providing an active, fail-to-safe site sensor for a fistula needle at an access site during hemodialysis; and automatically alerting medical personnel of a problem during hemodialysis using the active, fail-to-safe site sensor during at least the following: failing of the active, fail-to-safe site sensor; insufficient powering to the active, fail-to-safe site sensor; partial fistula needle dislodging from the access site; and complete needle dislodging from the access site.

11 Claims, 5 Drawing Sheets

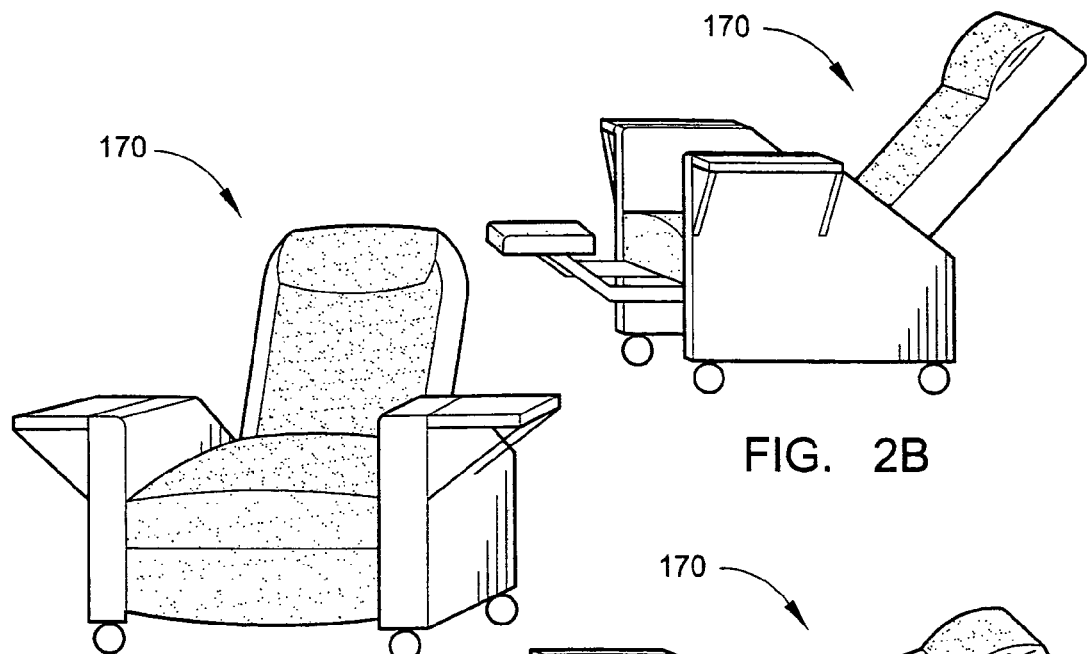
FIG. 2A
FIG. 2B
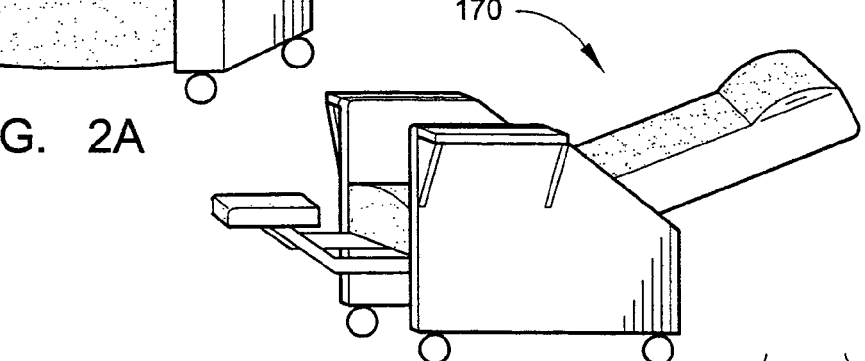
FIG. 2C
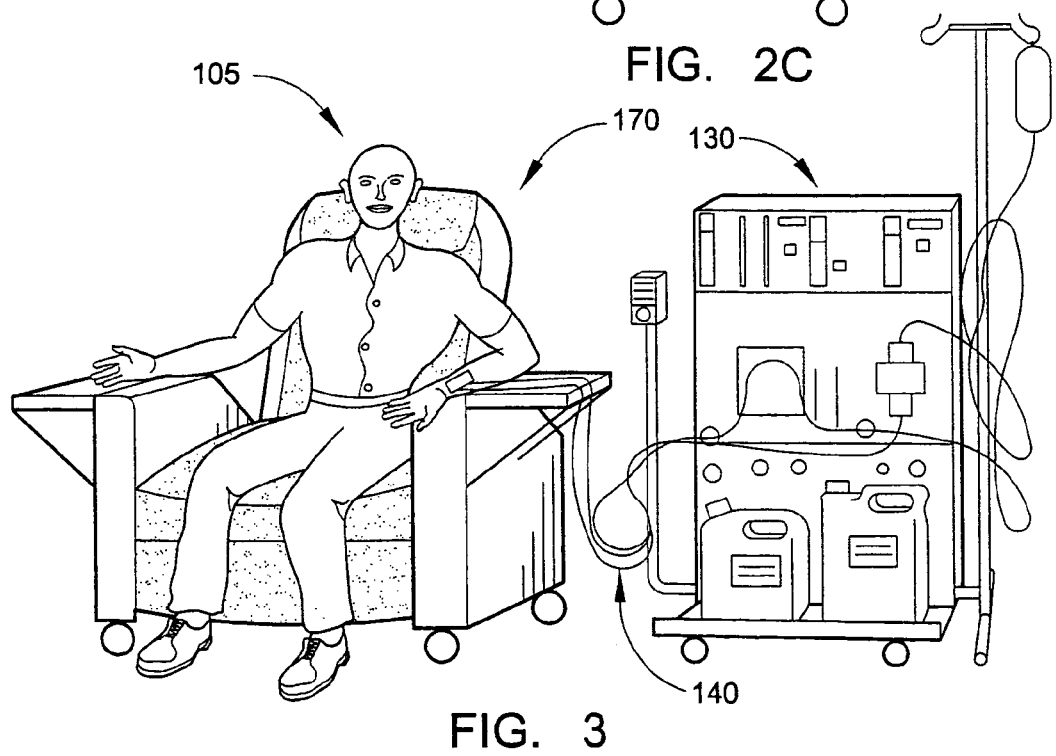
FIG. 3

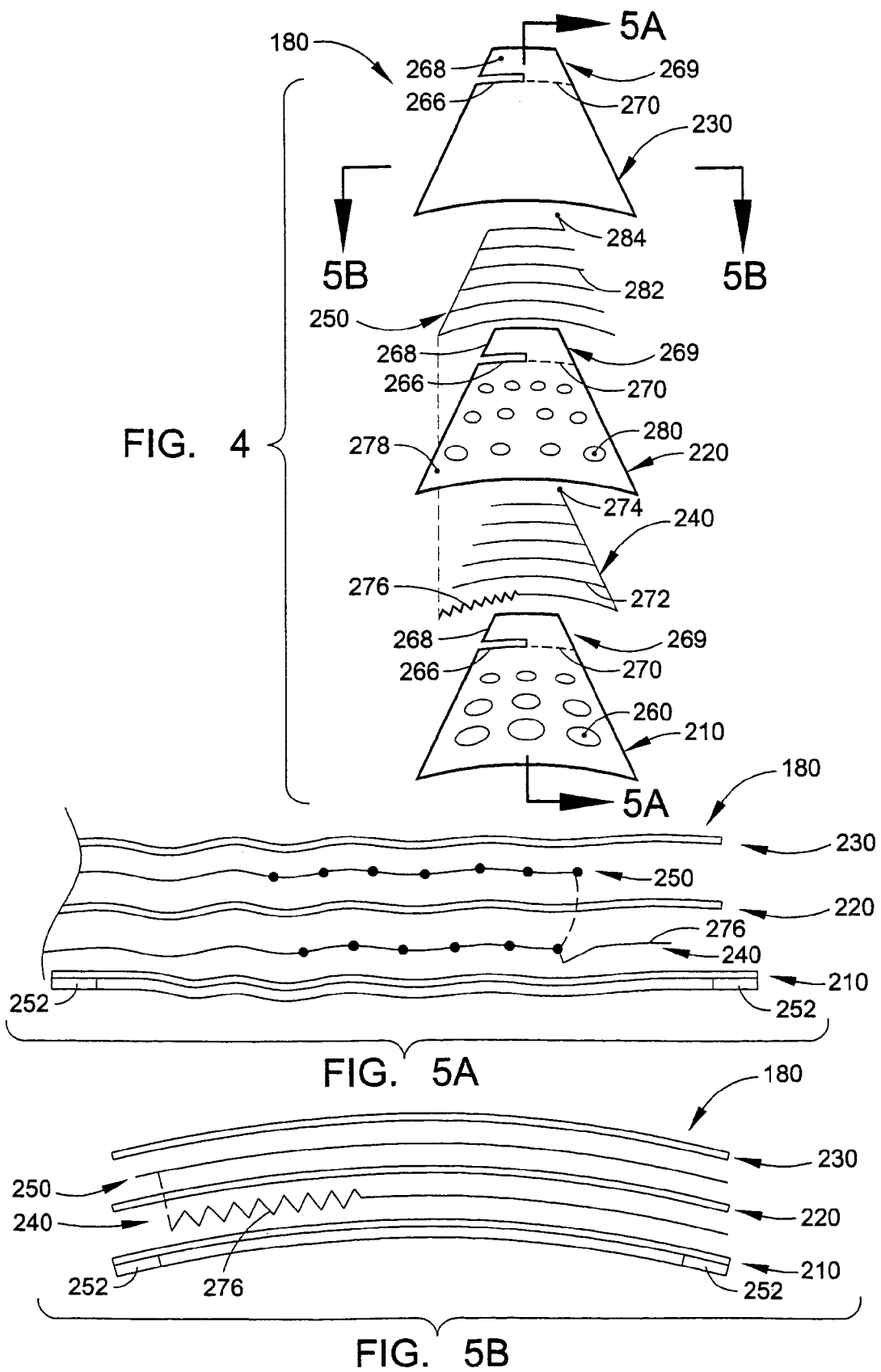

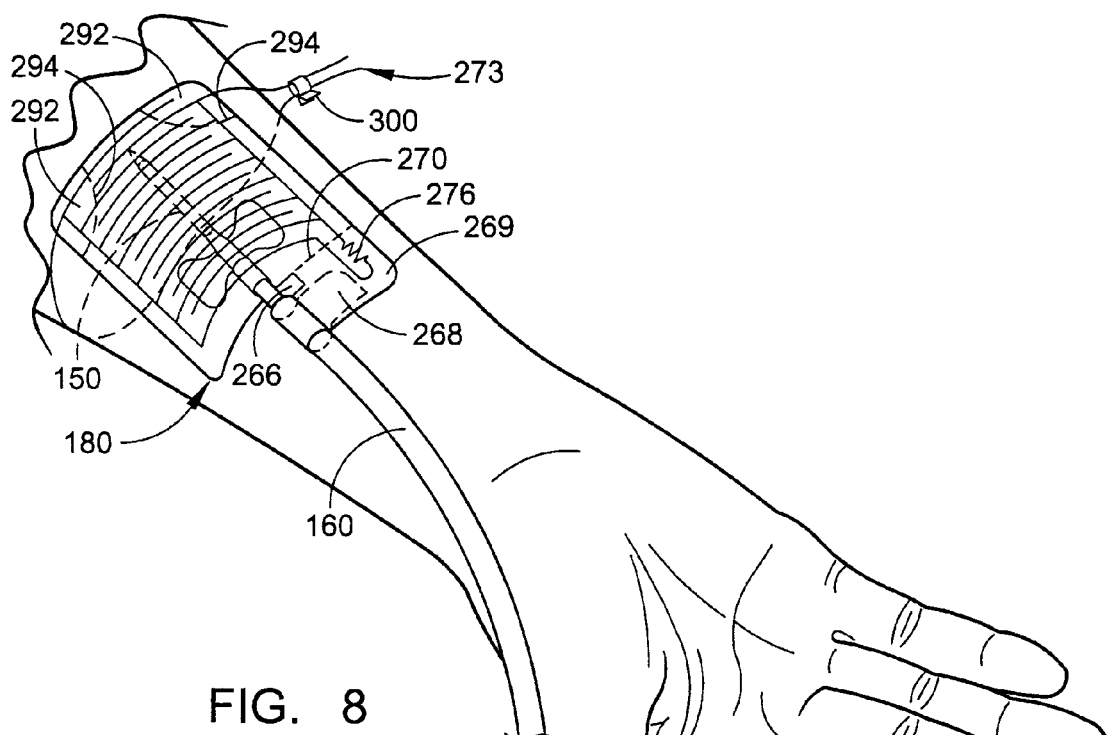
FIG. 8
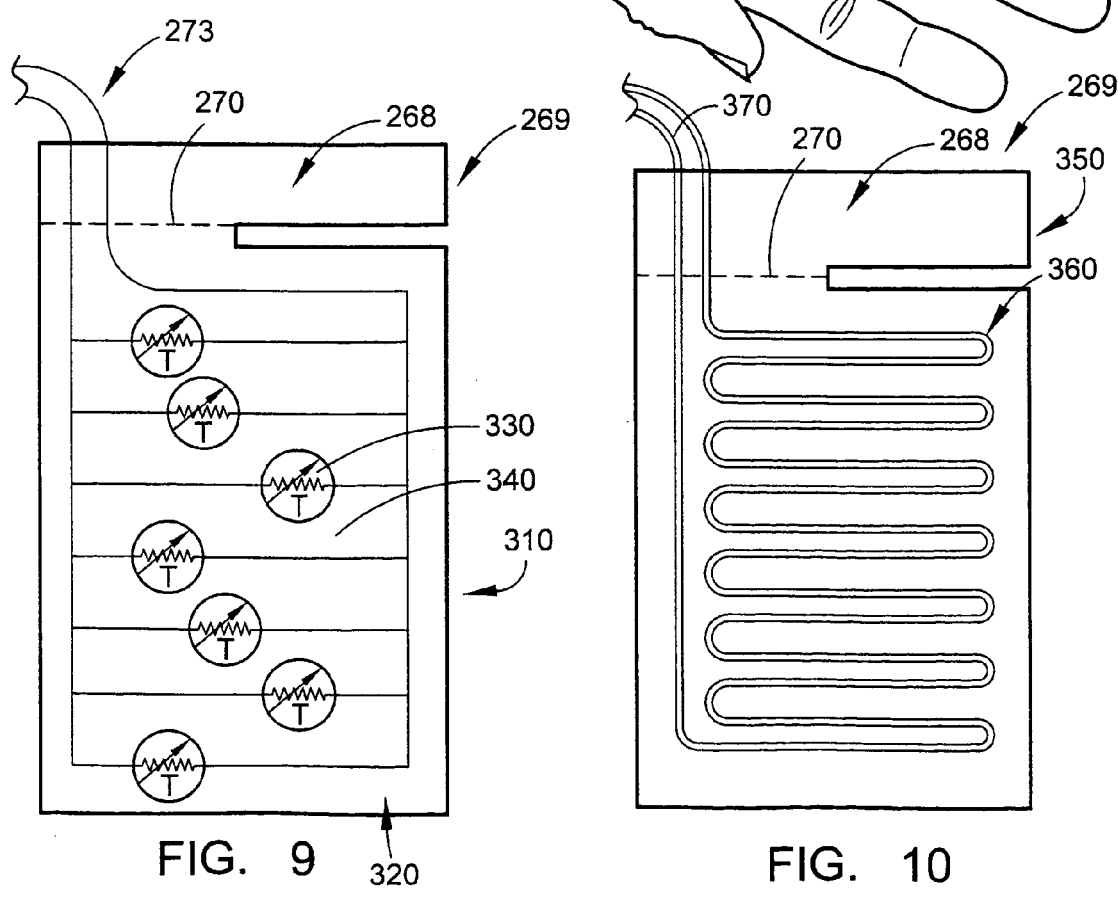
FIG. 9
FIG. 10

METHOD AND DEVICE FOR MONITORING LOSS OF BODY FLUID AND DISLODGMENT OF MEDICAL INSTRUMENT FROM BODY

FIELD OF THE INVENTION

The present invention is in the field of methods and devices for alerting medical personnel of the leakage of blood or other fluids from a medical instrument insertion site into the body and of the dislodgment of the medical instrument from the insertion site.

BACKGROUND OF THE INVENTION

A "fistula needle" is a large bore needle, commonly 14 to 17 gauge, which is bonded to a section of medical grade tubing used to connect the fistula needle to an extracorporeal blood circuit for use in hemodialysis.

Hemodialysis is one of the primary treatments for patients with kidney failure. These life-sustaining treatments typically require 3 to 4.5 hours each and may occur three or more times a week. However, due to differences in protocols, techniques, or varying patient needs, some hemodialysis treatment may last six hours or even overnight.

The most common access to the vascular system during hemodialysis, for chronic patients, is through use of a large gauge needle inserted through the skin into an arterial/ventricular graft, an implanted shunt or an implanted receptacle.

During a treatment, the patients' blood is processed by a filtering device commonly called a dialyzer or hemodialyzer. The blood travels to and from this filtering device through an extracorporeal blood circuit by the action of a blood pump. Every hemodialysis unit is required to have certain alarms (AAMI RD5-3.3.6) that monitor conditions throughout a treatment to insure patient safety. These alarms include temperature, dialysate pressure, transmembrane pressure, blood circuit pressure, conductivity, blood leak, and blood circuit air embolism protection.

Blood travels out from the body through the arterial fistula needle to an arterial bloodline. The arterial blood is then pumped through the bloodline, into and through the filtering device, and returned to the body through the venous bloodline attached to the venous fistula needle. As used herein, the term "venous" it is intended to mean "returning to the body" and the term "arterial" is intended to mean "coming from the body". These fistula needles are commonly taped in place on the patient's skin near and around the access site.

One or both of the fistula needles are occasionally dislodged or removed from the access site during a treatment. Some examples of how this hazardous situation may occur unintentionally include the bloodlines getting caught on the treatment chair during a positional change such as reclining from a seated position or siting up from a reclined position. Dislodgment may also occur when clothing or blankets brush against the fistula needles and tapings during normal movements. Sometimes someone moving past catches the bloodline with a foot, a walker, a wheelchair or a cart. It may even happen when the tape on a patient simply comes off, due to dry or sweaty skin, and the needles slip out. Intentional removal of the needle(s) during treatment is also not unheard of, requiring many of the more mentally or emotionally unstable patients to be restrained during treatments. Other patients move around frequently and the many little tugs on the bloodline and tapings, and the constant pulling eventually loosens that tapings to the point that they come off and the fistula needle falls out.

Should the venous needle become partially dislodged during a treatment, the patients' blood may infiltrate (into the surrounding tissue areas), usually causing great pain, or it may leak out around the needle entry site, or a combination of both.

Should the venous needle become completely dislodged during a hemodialysis treatment, the patients' blood is not being returned and the blood is effectively drained out. With typical blood pump ranges of 50 to 650 ml/min., the blood loss may be very rapid. This situation requires an immediate medical intervention response to prevent severe patient injury or death by exsanguination. Obviously, even the most observant and dedicated of medical staff could not possibly watch each patient all of the time.

Currently, the primary device to monitor for a venous needle dislodgment is the venous pressure monitor (VPM). Under certain circumstances, VPM is not a dependable indicator for a venous needle dislodgment because the VPM may not "see" a change beyond the standard alarm limit range (50 ml/min.). This may be exacerbated when the alarm limits are not set "centered" around the varying average pressure. Significantly, the VPM will often fail to register a sufficient pressure change (to set off an alarm) due to the inherent "back pressure" developed in a venous blood line by the resistance of the viscous blood traveling through the relatively small orifice of the fistula needle.

One attempt to solve the partial dislodgment problem is offered by Shaw in his U.S. Pat. Nos. 3,618,602 and 4,010,749. These basically use the increase in skin temperature to determine the presence of an infiltration. This solution has limitations in that it is rather slow to respond as it is dependent on the reaction of the body to the problem. Additionally, it fails to address the present concern of dislodgment. While an infiltration is painful, may require surgery to correct and could even result in the loss of the limb, it is not immediately life threatening.

One proposed solution to the complete dislodgment problem is attempted in U.S. Pat. No. 6,077,443, entitled "Method and device for monitoring a vascular access during a dialysis treatment", issued to Goldau, Rainer, which monitors the impulses (natural or added) detectable in an extracorprial blood circuit. This method has not experienced commercial success, or widespread utilization. It is believed this may be because the pressures illustrated appear to be on a very still patient, which is not a realistic assumption throughout a four-hour or longer treatment. Even very small arm movements can set off the VPM without dislodgment of a needle because of the natural pressures inherent in the needle as described above.

There are a number of sensor designs that use the inherent conductivity of blood and other fluids to set off an alarm, most commonly used in a diaper to indicate a soiled condition.

A "System for use in detection of electrically conductive fluids" was suggested in U.S. Pat. No. 5,790,036, issued to Fisher, et al., which uses the inherent conductivity of body fluids and wastes to set off an alert in a diaper. This arrangement does not adequately protect a patient as it could have a sensor failure or disconnect without alerting the staff of the sensor failure or disconnection. Additionally, the device does not explicitly provide for compliance with the nonisolated patient connection requirements of Safe Current Limits for Eletromedical Apparatus as required by Applicable Document 2.3.

U.S. Pat. No. 5,779,657 to Daneshvar entitled "Non-stretchable wound cover and protector" shows and describes a simple blood leak detector. The soiling of a gauze pad with blood would complete a circuit, allowing an alarm to sound. As in the case of the Fisher unit, Daneshvar's unit fails to alarm in the case of a sensor failure. Daneshvar's unit also is not compliant with the nonisolated patient connection requirements for electrically sensitive patients. Additionally, whether Daneshvar's unit will alarm depends on the absorbency of the gauze, which may be compromised due to being saturated by non-conductive fluids or by compression, or coated by certain medical gels, pastes or ointments.

The devices described in WO 99/24145 and U.S. Published Patent Application 2002/0198483 A1 attempt to detect a separation of the extracorporeal circuit. However, neither of these allow for an unobstructed view of the access site. Another problem they share is that they are designed for use as an integral part of a dialysis machine. As such, they are specifically not designed for stand-alone use. Of greater concern is the failure of any of these devices to fail in a safe manner. If the unit fails for some reason, such as a dead battery, the protection is lost and the staff is not aware of it. While both of these references indicate that they determine needle dislodgment, they really are mere variations on the wet diaper sensor idea in that they only detect blood or other conductive fluids. They are not actually determining the needle position. With some of the newer implanted tubing and other new types of vascular accesses, there is very little bleeding when a needle is removed, and, hence, limited opportunity for success in alerting the staff in the case of a rapid needle withdrawal, such as when a bloodline is caught by a passing foot, or when a mentally unstable patient intentionally removes the needle. Additionally, in applications other than dialysis, the underlying region or substrates may not have a sufficient positive relative pressure to force out blood, body fluid or liquid to wet the sensor.

The reusable sensors described in the references mentioned above and elsewhere in the prior art involve the myriad of problems and costs associated with reusing soiled medical equipment including, but not by way of limitation, sterilization, clean storage, verification of the absence of the sterilant prior to use, reused devices being reused only by the original patient, quality problems due to subjective assessments, etc.

SUMMARY OF THE INVENTION

The present invention involves a device for monitoring loss of body fluid and dislodgment of a medical instrument from an access site of the body. The device involves a system that is designed for use as a critical medical monitor, provides the requisite electrical isolation, and provides an unobstructed view of the access site. The device incorporates a sterile and disposable sensor that fails-to-safe such that a loss of protection results in an alarm, can be reset in the case of small leaks, can be tested "in-situ", without extra test equipment, alarms if the patch is removed or damaged in use, can stand alone and is not be required to be integrated into the alarm circuits of common, existing hemodialysis units, monitors the placement of the needle relative to its insertion point, has a monitored power supply, and alarms in the intentional removal of needle by patient.

Another aspect of the invention involves a hemodialysis site sensor attachable to at least one of a blood line and a fistula needle for alerting medical personnel of the leakage of blood from an access site where the fistula needle enters into a patient's body and dislodgment of the fistula needle from the access site. The hemodialysis site sensor includes a base membrane layer made of a medical-grade, biocompatible material and including an upper side, a lower side adherable to skin of the patient, and one or more holes disposed therein to allow the passage of blood and vapor therethrough; a first membrane layer including an upper side, a lower side, and one or more holes disposed therein to allow the passage of blood and vapor therethrough; a third membrane layer including an upper side and a lower side; an electrical connection adapted to be electrically coupled to an analytical circuit and including a first sensing array disposed between the upper side of the base membrane layer and the lower side of the first membrane layer, a second sensing array disposed between the upper side of the first membrane layer and the lower side of the third membrane layer, and resistively connected to the first sensing array; a disconnection mechanism attachable to at least one of the blood line and the fistula needle and severing the electrical connection upon dislodgment of the fistula needle from the access site; and wherein an electrical signal sent through the electrical connection changes when blood contacts at least one of the sensing arrays or the electrical connection is severed by the disconnection mechanism, causing the analytical circuit to actuate an alarm notifying medical personnel of partial or total dislodgment of the fistula needle from the access site.

Another aspect of the invention involves a method of alerting medical personnel of partial and total dislodgment of a fistula needle from an access site where the fistula needle enters into a patient's body during hemodialysis. The method includes providing a site sensor including a base membrane layer made of a medical-grade, biocompatible material and including a lower side adherable to skin of the patient at the access site, and one or more holes disposed therein to allow the passage of blood and vapor therethrough, a top membrane layer, an electrical connection including one or more resistively connected sensing arrays disposed between the base membrane layer and the top membrane layer, and a disconnection mechanism attachable to at least one of the blood line and the fistula needle and severing the electrical connection upon dislodgment of the fistula needle from the access site; providing an analytical circuit in electrical communication with the electrical connection; sending a signal from the analytical circuit to the site sensor and receiving the signal from the site sensor with the analytical circuit, the signal traveling through the one or more resistively connected sensing arrays of the electrical connection; partially dislodging the fistula needle from the access site causing blood to contact the one or more resistively connected sensing arrays and the signal sent from the analytical circuit to change; completely dislodging the fistula needle from the access site causing the disconnection mechanism to sever the electrical connection and the signal sent from the analytical circuit to change; determining with the analytical circuit whether the signal changed outside of a predetermined range; and actuating an alarm with the analytical circuit if the signal changed outside of a predetermined range.

A still further aspect of the invention involves a method of alerting medical personnel of a problem during hemodialysis. The method includes providing an active, fail-to-safe site sensor for a fistula needle at an access site during hemodialysis, for a needle, or for another skin penetrating medical device; and automatically alerting medical personnel of a problem during hemodialysis using the active, fail-to-safe site sensor during at least the following: failing of the active, fail-to-safe site sensor; insufficient powering to the active, fail-to-safe site sensor; partial fistula needle dislodging from the access site; and complete needle dislodging from the access site.

Further objects and advantages will be apparent to those skilled in the art after a review of the drawings and the detailed description of the preferred embodiments set forth below.

BRIEF DESCRIPTION OF THE DRAWINGS

FIG. 2A is front perspective view of an embodiment of a dialysis treatment chair in a normal position.

FIG. 2B is right perspective view of the dialysis treatment chair of FIG. 2A and illustrates the chair in a reclined position.

FIG. 2C is right side elevational view of the dialysis treatment chair of FIG. 2A and illustrates the chair in a fully reclined, Trendlenburg position.

FIG. 3 is a front perspective view of an embodiment of a hemodialysis unit connected to a dialysis patient sitting in a dialysis treatment chair.

FIG. 4 is an exploded perspective view of an embodiment of a site sensor of the system for monitoring loss of body fluid and dislodgment of a medical instrument from an access site of the body.

FIG. 5A is a cross-sectional view of the site sensor taken along lines 5A—5A of FIG. 4.

FIG. 5B is a cross-sectional view of the site sensor taken along lines 5B—5B of FIG. 4.

FIG. 8 is a perspective view of an alternative embodiment of a site sensor applied to a patient's arm with a fistula needle/bloodline of an extracorprial blood circuit and conductive wires shown extending from the site sensor.

FIG. 9 is a top plan view of another embodiment of a site sensor.

FIG. 10 is a top plan view of a further embodiment of a site sensor.

DETAILED DESCRIPTION OF PREFERRED EMBODIMENTS

With reference to FIGS. 1–10, an embodiment of a system and method for monitoring a vascular access site of a patient 105 during a hemodialysis treatment and alerting the medical staff in the event of a needle dislodgment will be described.

Although the system will be described in conjunction with monitoring a vascular access site during a hemodialysis treatment, the system may be used for monitoring any penetration or access site through the skin with respect to blood, body fluids, and/or medical fluids that may leak around the skin penetration site and/or dislodgment of a needle relative to the skin penetration or access site. Further, the system may be used for monitoring access of the vascular system, access to sub-dermal or other implanted devices, access of the peritoneal cavity, access of internal organs, monitoring trans-dermal exudation, other usage where an alert to the leakage of blood, body fluids, medical fluids, liquids or other fluids may be desired, or other usage where an alert to the separation of a medical device or instrument from an access site of the human body may be desirable.

Before describing the system in detail, hemodialysis and some of the equipment used during hemodialysis will first be described.

Figure 1:
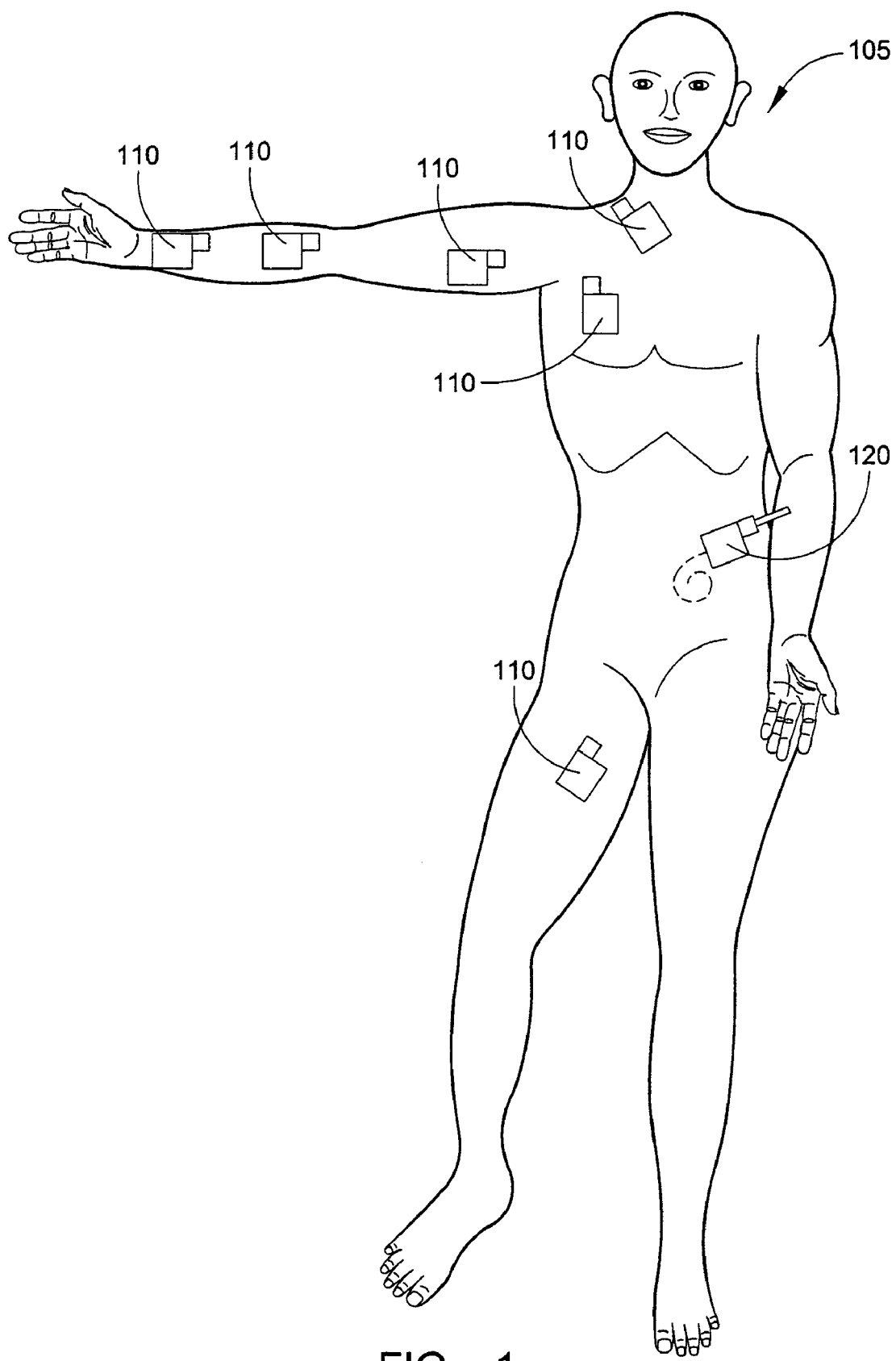
FIG. 1 is a front elevational view of a human and illustrates multiple exemplary vascular and peritoneal access sites.

Hemodialysis is one of the primary treatments for patients 105 with kidney failure. These life-sustaining treatments typically require 3 to 4.5 hours each and may occur three times a week. The most common access to the vascular system, for chronic patients, is through use of a large gauge needle inserted through the skin into an arterial/ventricular graft, an implanted shunt or an implanted receptacle at one of the common sites 110 (FIG. 1) used for access to the vascular system of the patient 105. While the illustrated sites in FIG. 1 are not exhaustive, these sites are the normal locations for accessing the blood supply for use in hemodialysis and apheresis as well as where the interventional radiologist accesses the primary blood vessels for access to the heart. Several of these locations are viable for infusion therapy as well.

The use of medical tape and a patch of sterile gauze covering the peritoneal insertion site 120 should be noted because this is an example of a site that may be monitored by the system in an alternative embodiment for any leakage, bleeding, or oozing which would indicate infection.

During a treatment, the blood of the patient 105 is processed by a hemodialysis unit 130 (FIG. 3). The blood travels to and from the hemodialysis unit 130 through bloodlines 140 of an extracorporeal blood circuit by the action of a blood pump in the hemodialysis unit 130.

Blood travels out from the body through an arterial fistula needle 150 (FIG. 6) to an arterial bloodline 160, which may be connected to the arterial fistula needle 150 by a leader and appropriate luer lock fittings. The arterial blood is then pumped through the arterial bloodline 160, into and through the hemodialysis unit 130, and returned to the patient 105 through a venous bloodline attached to a venous fistula needle.

During the dialysis process, the patient 105 normally rests in a typical dialysis treatment chair 170 (FIGS. 2A–3) in one of three positions: 1) a normal sitting position (FIG. 2A), 2) a reclined sitting position (FIG. 2B), and 3) a fully reclined or Trendelenburg sitting position (FIG. 2C). The fully reclined position or Trendelenburg sitting position shown in FIG. 2C is used to lower the head of the patient 105 below the level of the heart and is used when the blood pressure of the patient 105 gets too low ("crashing") and staff is attempting to prevent the patient 105 from blacking out. It is important to note the many corners of the chair 170 and other features of the chair 170 that provide opportunities for the needle 150 to be pulled on when changing from one sitting position to another. Bloodlines 140 may get caught on the treatment chair 170 during a positional change such as reclining from a seated position or sitting up from a reclined position, causing one or both of the fistula needles to become partially or completely dislodged or removed from the access site during dialysis. Dislodgment may also occur when clothing or blankets brush against the fistula needles and tapings during normal movements by the patient 105.

It is also important to notice that, as with most chairs, the sides of the chair 170 are covered, which often greatly increases the time between when the needle 150 is dislodged and when it is noticed by the medical staff by observation of a growing puddle of blood on the floor under the expiring patient 105. The presence of sides on dialysis chairs 170 also causes the problem of clothing or blankets tending to bunch up in the lower corners of the chair 170, soaking up blood that is leaking—again extending the time between when the needle 150 is dislodged and when it is noticed by the medical staff.

The drawing of FIG. 3 illustrates how the bloodlines 140 dangle between the chair 170 and the hemodialysis unit 130 during the typical dialysis process, and the danger this represents due to the fistula needles and bloodlines 140 being accidentally caught and pulled from the patient 105 during dialysis due to the length of the bloodlines and their potential for interference with the medical attendants that serve the patient 105 undergoing dialysis. In certain situations, such as when a dialysis treatment station is positioned in a corner, the hemodialysis unit 130 may be on the side of the patient 105 opposite the patient's access to the chair 170. In this case, the bloodlines 140 actually cross over the patient 105, significantly increasing the risk of having the bloodlines 140 being inadvertently caught on something or pulled on. Sometimes someone moving past catches the bloodlines 140 with a foot, a walker, a wheelchair or a cart.

Should the venous needle become partially dislodged during dialysis, the blood of the patient 105 may infiltrate (into the surrounding tissue areas), usually causing great pain, or it may leak out around the needle entry site, or a combination of both.

Should the venous needle become completely dislodged during a hemodialysis treatment, the blood of the patient 105 is not being returned and the blood is effectively drained out. With typical blood pump ranges of 50 to 650 ml/min., the blood loss may be very rapid. This situation requires an immediate medical intervention response to prevent severe patient injury or death by exsanguination.

Figure 6:
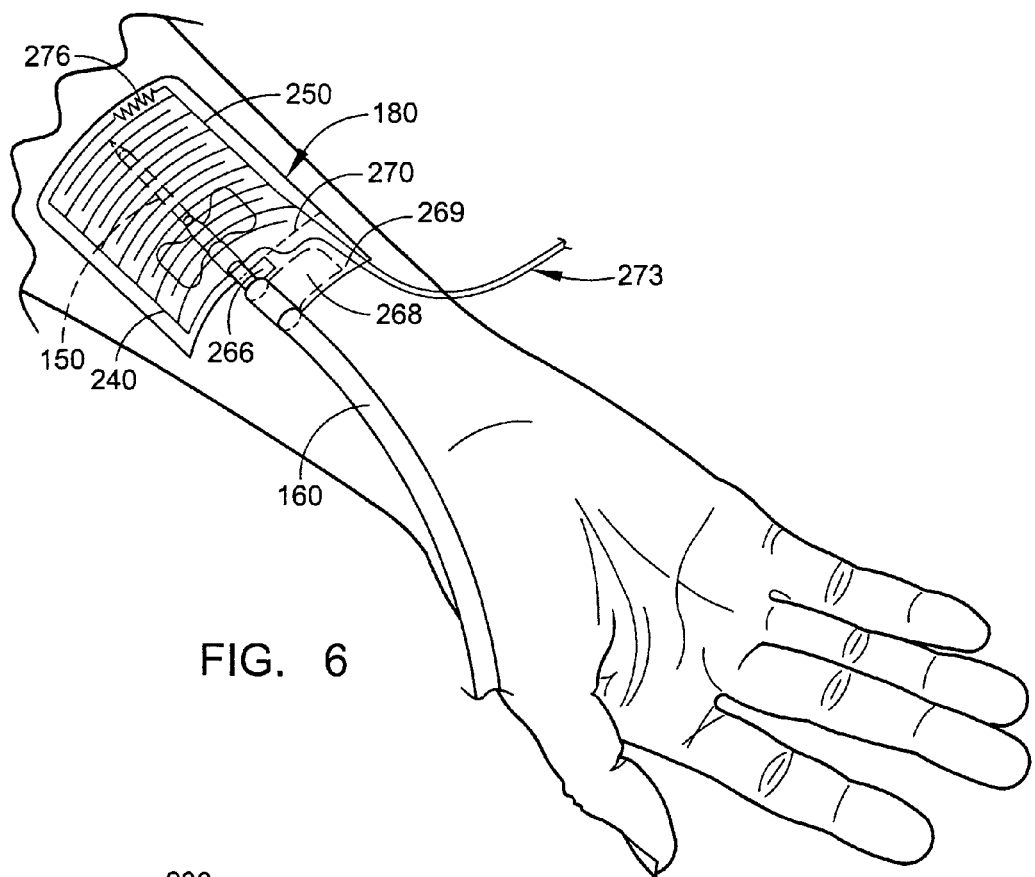
FIG. 6 is a perspective view of the site sensor of FIG. 4 applied to a patient's arm with a bloodline of an extracorprial blood circuit and conductive wires shown extending from the site sensor.
Figure 7:
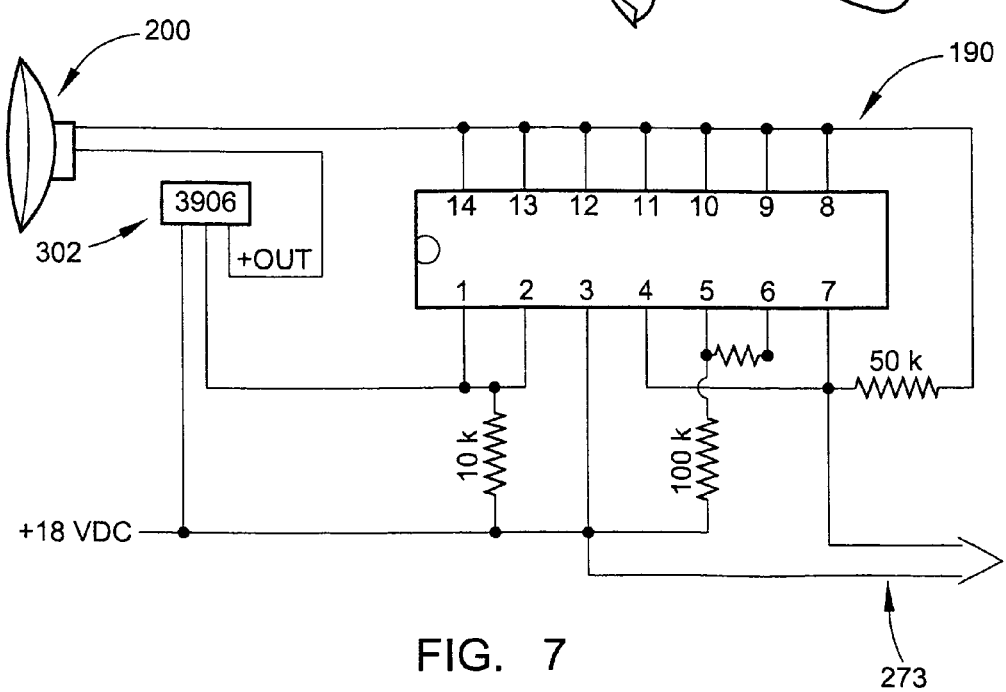
FIG. 7 is an electrical schematic of an embodiment of an analytical circuit and enunciator that may be used with the site sensor.

With reference to FIGS. 4–7, the system will first be generally described followed by a detailed description of the elements of the system. The system generally includes a site sensor 180 (FIGS. 4–6), an analytical circuit 190 (FIG. 7), and an enunciator 200 (FIG. 7). A electrical signal is sent from the analytical circuit 190 to the active site sensor 180, where the signal passes through one or more sensing arrays of the site sensor 180, and back out to the analytical circuit 190. The analytical circuit 190 monitors the return signal. Any change of this returned signal outside of a designated range produces an alarm output, which is coupled to the enunciator 200, for alerting medical personnel. The site sensor 180 includes a disconnection mechanism that disconnects the site sensor 180 from the analytical circuit 190 upon sufficient pull of the bloodline 160. This changes the returned signal to the analytical circuit 190, producing an alarm output that is sent to the enunciator 200 for alerting medical personnel.

Each of main elements of the system will now be described in more detail in turn below:

Site Sensor:

With reference to FIGS. 4–6, the embodiment of the site sensor 180 shown includes a base membrane layer 210, a second membrane layer 220, and a third membrane layer 230. A first conductive layer or sensing array 240 is disposed between the base membrane layer 210 and the second membrane layer 220, and a second conductive layer or sensing array 250 is disposed between the second membrane layer 220 and the third membrane layer 230. Although the sensing arrays 240, 250 are shown separated by the single second membrane layer 220, in an alternative embodiment, the sensing arrays 240, 250 may be separated by more than one layer and/or may have additional sensing layers between them.

The base membrane layer 210 is made up of one or more appropriate medical-grade, biocompatible materials, and have a rectangular shape as shown or may have a different shape. The same may be true for the other membrane layers 220, 230. An underside of the base membrane layer 210 may be completely or partially coated or circumscribed with a coating of medical-grade, biocompatible adhesive 252 (FIGS. 5A, 5B) covered by a removable sheet to allow for the attachment of the site sensor 180 to the prescribed area on the patient 105. The adhesive may include one or more adhesives of different adhesive strengths to facilitate controlled separation of the site sensor 180 along prescribed lines 270 or at the connector of the site sensor 180 in a manner to be described device when a dislodging stress is applied to the bloodline 160 to interrupt the signal being transmitted through the site sensor 180 and cause an alarm condition. The site sensor 180 may also be held in place by any number of methods, as known to those skilled in the art, in conjunction with or in place of the medical-grade, biocompatible adhesive. The locational stability of the site sensor 180 is of paramount importance to the functional benefit of the system. The site sensor 180 in every case must be firmly attached to the fistula needle 150 and/or the bloodline 160. This attachment may be made during manufacturing, attached at time of use, or sometime in between.

In an alternative embodiment, the base membrane layer 210 may carry one or more electrodes somewhat below the base membrane layer 210 to indicate positive contact with the skin of the patient 105. An exemplary electrode that may be used for this purpose is a silver/silver-chloride type as is used in a plethysmograph or an ElectroCardioGram (ECG) lead set; however, other types of electrodes, as is known to those skilled in the art, and/or additional sensors may be used. The one or more electrodes and/or sensors may be coupled to the first sensing array 240 or have another electrical connection for the purpose of determining actual physical contact with the skin of the patient 105. The first sensing array 240 may, if placed below the base membrane layer 210 or in the absence of the base membrane layer 210, provide a biorhythm output (e.g., an ECG waveform may be transmitted to the analytical circuit 190) that is indicative of a good and stable connection with the patient 105. An additional advantage of this is that if the patient expires, thus ending the waveform, an alarm at the enunciator 200 may be actuated.

The base membrane layer 210 may have holes 260 to allow for the free passage of perspiration, blood, other liquids and/or vapors through the layer. One of more of these holes 260 may be of the same or varying sizes, shapes, quantities and regional densities. The base membrane layer 210 (and the other membrane layers 220, 230) may have a perforation 270, or other preconditioning treatment, along a prescribed path to facilitate the destruction of the site sensor 180 along prescribed lines in the case of a physical force against it from a pull on the bloodline 160 or fistula needle, again resulting in an alarm state. The perforation 270 may terminate in a generally rectangular cut-out 266, which delineates a pull-over adhesive tab 268 of a detachment section 269. The adhesive tab 268 may include an adhesive covered by removable sheet on its upper surface. The pull-over adhesive tab 268 and the perforation 270 combine to form a dislodgment mechanism. In alternative embodiments, the dislodgment mechanism may have alternative configurations, different elements, and/or greater or fewer elements. With reference to FIG. 6, in use, bloodline 140 and/or fistula needle 150 is placed through the cut-out 266, over the adhesive tab 268 and under the rest of the site sensor 180, the removable sheet is removed from the adhesive tab 268, exposing the adhesive, and the adhesive tab 268 is folded over the bloodline 140 and/or fistula needle 150 and adhered to the upper surface of the third membrane layer 230 so that the bloodline 140 and/or fistula needle 150 is firmly attached to the tab 268 such that a pull on the bloodline 140 would separate the conductive wires 272 or connection 284 and detachment section 269 from the rest of the site sensor 180 along the perforation 270, thus interrupting the conductive path and causing the analytical circuit 190 to cause the actuation of an alarm at the enunciator 200.

An upper side of the base membrane layer 210 may be used as a base for the first sensing array 240 to be placed, painted, deposited, adhered to, or otherwise disposed on. The first sensing array 240 may be held between the base membrane layer 210 and the second membrane layer 220, and include a plurality of conductive wires or traces 272. One of conductive wires 273 (FIG. 6) connecting the site sensor 180 and the analytical circuit 190 may be connected to the first sensing array 240 at a connection point 274 (FIG. 4) at one end of the first sensing array 240. One or more resistors 276 may be located at an opposite end of the first sensing array 240 and may be used to resistively connect the first sensing array 240 to the second sensing array 250 through a hole 278 in the second membrane layer 220. The first sensing array 240 may have a configuration and be positioned so as to evenly cover the area between the base membrane layer 210 and the second membrane layer 220. The first sensing array 240 may cover some, all, or none of the holes 260 in the base membrane layer 210. The first sensing array 240 may be embedded in one of the layers 210, 220, or may be simply attached to or held in place between the layers 210, 220. The first sensing array 240 may be of one polarity or made up of multiple leads with several polarities.

The second membrane layer 220 may also have holes 280, one or more of which may be of the same or varying sizes, shapes, quantities and regional densities.

These holes 280 may or may not line up with the holes of any other layer. The top of the second membrane layer 240 may be used as a base for the second sensing array 250 to be placed, painted, deposited, adhered to, or otherwise disposed on. The second sensing array 250 may be held between the second membrane layer 220 and the third membrane layer 230, and include a plurality of conductive wires or traces 282. One of the conductive wires 273 connecting the site sensor 180 and the analytical circuit 190 may be connected to the second sensing array 250 at a connection point 284 at one end of the second sensing array 250 by soldering or any other well-known electric connection manner. These connectors may be of a calibrated strength or holding ability. The second sensing array 250 is connected to the one or more resistors 276 at an opposite end of the second sensing array 250. The second sensing array 250 may have a configuration and be positioned so as to evenly cover the area between the base membrane layer 210 and the second membrane layer 220. The second sensing array 250 may cover some, all, or none of the holes 280 in the second membrane layer 220. The second sensing array 250 may be embedded in one of the layers 220, 230, or may be simply attached to or held in place between the layers 220, 230. The second sensing array 250 may be of one polarity or made up of multiple leads with several polarities.

The sensing arrays 240, 250 are preferably resistively connected through the one or more resistors 276, allowing for the fail-to-safe feature of the present invention, which will be described in more detail below. In alternative embodiments, the wires or traces of both arrays 240, 250 may be made of a resistive material.

Although the sensing arrays 240, 250 have been described as having a configuration and being positioned so as to evenly cover the area between the layers 210, 220, 230, the coverage of the areas by the sensing arrays 240, 250 may not necessarily be even. In alternative embodiments, differing amounts of coverage in differing areas may occur. For example, a space may be located near the center of the site sensor 180 to allow penetration through the site sensor 180 without damaging, disturbing, or contacting any of the sensing arrays 240, 250.

The third membrane layer 230 is also made of one or more appropriate medical-grade, biocompatible materials. The third membrane layer 230 preferably does not include holes like the base membrane layer 210 and the second membrane layer 220, but is preferably made of one or more appropriate materials to allow for the transpiration of perspiration and vapor, but not blood or other liquids. This selectively or semi-permeable layer 230, together with the seal formed by the adhesive of the base membrane layer 210, ensures that the sensing arrays 240, 250 will come into contact with any blood or liquids that may be coming from the protected area.

Outer edges of the membrane layers 210, 220, 230 may be sealed, glued or bonded to one-another in any manner as known to those skilled in the art.

The site sensor 180 is preferably transparent in all of the one or more layers above the needle entry site.

With reference to FIG. 8, an alternative embodiment of the site sensor 180 is shown where conductive leads 273 connect with the site sensor 180 at detachment corner sections 292 near an end of the site sensor 180 opposite the detachment section 269 and wrap around the limb of the patient. A cinching mechanism 300 may be used to cinch the conductive leads 273 snugly against the limb to help to make the physical location and security of the site sensor 180 against the limb more stable. The bloodline 160 is secured to the site sensor 180 by the adhesive tab 268 of the detachment section 269 in a manner similar to that described above with respect to FIGS. 4–6 so that the force that would dislodge the fistula needle 150 causes the adhesive tab 268 and detachment section 269 to tear away from the site sensor 180 along the perforation 270 and interrupt the conductive path which would be detected by the analytical circuit 190, producing an alarm. Similarly, the force that would dislodge the fistula needle 150 (or movement of the patient's arm) may cause the site sensor 180 and one or both of the detachment corner sections 292, which are adhered strongly to the patient's skin, to separate along one or both perforations 294. This would interrupt the conductive path which would be detected by the analytical circuit 190, producing an alarm. In alternative embodiments, one or both of the perforations 276, 294 of the site sensor 180 may have a straight, rectilinear, or curvilinear configuration other than that shown.

In an alternative embodiment where the site sensor 180 is not used, one could simply wrap a wire similar to the conductive leads 290 around the limb of the patient and secure the wire to the fistula needle 150 to provide for an indication of needle dislodgment without leak detection because pulling on the bloodline 160 causes the wire to sever and interrupt the conductive path which would be detected by the analytical circuit 190, producing an alarm. In this embodiment, it would be desirable to secure the wire onto the limb with medical tapes, patches or manner known to those skilled in the art.

In the immediate following paragraphs, features that may be part of one or more of the implementations of the system or site sensors 180, 310, 350 (hereinafter "site sensor 180") described herein are indicated.

For example, in one or more implementations of the system, the system may include one or more of the following. The entire system is contained in a single unit. One or more of the site sensor 180, the analytical circuit 190 and the enunciator 200 are integrated with each other. The system is used for monitory blood/fluid leakage and/or needle dislodgment of at an access site of a human or animal. The site sensor 180, the analytical circuit 190 and the enunciator 200 are connected to each other with any mechanical connection device. The site sensor 180, the analytical circuit 190 and the enunciator 200 are connected to each other with any electrical connection device. The site sensor 180, the analytical circuit 190 and the enunciator 200 are connected to each other with any hollow fiber or solid fiber device. The site sensor 180, the analytical circuit 190 and the enunciator 200 are connected via any telemetering type equipment. The site sensor 180, the analytical circuit 190 and the enunciator 200 are connected via any optical/photonic type equipment. The site sensor 180, the analytical circuit 190 and the enunciator 200 are connected via any combination of equipment type. The site sensor 180 and enunciator 200 are controlled by a separate, distinct controller. The site sensor 180 has a series of tabs at the edges that have the connective areas of the conductive traces or leads. The site sensor 180 has a series of tabs at the edges that have the connective areas of the conductive traces or leads with fold-over tabs that complete the circuit such that all tabs are folded over (with self adhesive contacts) thus continuing the circuit, terminating at the one corner or tab where the actual connector leading to the analytical circuit 190 or enunciator 200 (or a combination of the two) is located. The site sensor 180 has a series of conductive rings that surround the exterior of the site sensor 180 such that a connector could be attached at any part of the edge of the site sensor 180 and make full contact with the required leads of the sensing array. The site sensor 180 utilizes a stereo or other style plug with as many discrete contacting areas as necessary. The site sensor 180 has a contact or connector at each level which may or may not be interconnected to each other (allows for various levels to be active). The site sensor 180, sensor/analytical circuit, or sensor/analytical circuit/enunciator assembly is self-adhesively attached to, or in position on, the monitored site on the subject. The site sensor 180, sensor/analytical circuit, or sensor/analytical circuit/enunciator assembly which is self-adhesively attached to, or in position on, the monitored site on the subject has an adhesive that is varied in its relative adhesive strength in order to facilitate destruction of the site sensor 180 along prescribed paths. The site sensor 180, sensor/analytical circuit, or sensor/analytical circuit/enunciator assembly is attached to, or in position on, the monitored site on the subject with one or more of (a) an arrangement of material(s), fibers, plastics, tubing, straps, or other useful product or device, tied, connected, bonded or otherwise joined so as to hold the site sensor 180, sensor/analytical circuit, or sensor/analytical circuit/enunciator assembly in contact with, or in position on, the monitored site of the subject; (b) an arrangement of adhesive tapes which may or may not be directly connected to the site sensor 180, sensor/analytical circuit, or sensor/analytical circuit/enunciator assembly in contact with, or in position on, the monitored site of the subject; (c) a clamp arrangement so as to physically hold the site sensor 180, sensor/analytical circuit, or sensor/analytical circuit/enunciator assembly in contact with, or in position on, the monitored site of the subject; (d) any combination of the methods (a), (b), and/or (c) so as to hold the site sensor 180, sensor/analytical circuit, or sensor/analytical circuit/enunciator assembly in contact with, or in position on, the monitored site of the subject. The power supply and analytical circuit 190 are contained within a dialysis unit. The power supply and analytical circuit 190 are contained within an apheresis unit. The power supply and analytical circuit 190 are contained within an infusion unit. The power supply and analytical circuit 190 are contained within a medical instrument or other medical device. The power supply and analytical circuit 190 are contained within an infusion pump unit. The site sensor 180 is connected to the analytical circuit 190 and/or enunciator assembly with a conductive wire, set of wires, coiled wire set or any other form of conductive wiring or cable as know to those skilled in the art. The site sensor 180, sensor/analytical circuit, or sensor/analytical circuit/enunciator assembly is attached to seat, bed, mattress, float, cushion, gurney, wheelchair, or any other physical device for support of the patient. The site sensor 180, sensor/analytical circuit, or sensor/analytical circuit/enunciator assembly is attached to the floor, ceiling, wall, post, column, bar, or any other physical structure on, around or near the patient.

In one or more implementations of the site sensors 180, 310, 350, the site sensors 180 may include one or more of the following. There may be other numbers of layers of material and varying areas covered by one or more sensing arrays, which may have their own electrical connector, so that differing volumes of liquid are required to generate an alarm. There may be concentric areas of sensing arrays to allow for multiple levels of protection or to allow resetting of the system without having to use a new site sensor 180. The site sensor 180 may include a test section to allow for functional verification of the site sensor 180. The site sensor 180 may allow for oblique and/or perpendicular piercing of the site sensor 180 by one or more needles and may allow for the attachment of the one or more needles in the manner shown and described above. Such an embodiment would be ideal for use with the devices implanted in the upper chest or clavicle area such as the Vasca device, for such items as drainage tubing as used in many surgeries, and for use with indwelling catheters and central line catheters and the like. The space or gap between the layers 210, 220, 230 may be varied or function as the calibrated variable in determining how much blood or other fluid is required to set off the alarm in the site sensor 180. One or more drain holes may be included in the site sensor 180 to allow blood or other occluding fluid that may have set off the alarm to be cleared. After the fistula needle 150 has been repositioned, a press on the top of the site sensor 180 would cause the displacement of the blood or occluding fluid out of the one or more drain holes, which may have a valve or other flow control device, and allow the continued use of the site sensor 180 without having to replace it. This would be of significant advantage in the case of a larger sized site sensor 180 such as a site sensor 180 for larger wound coverings or for monitoring shunts such as those used in radiographic heart studies (angiograms, angioplasty, etc.). Alternatively, the site sensor 180 may include a "luer lock" or other tubing or syringe connector to allow the use of nonconductive sterile water or even air to rinse the site sensor 180 out in-situ. In such an embodiment, the third membrane layer 230 may have one or more vent holes to facilitate this.

In one or more implementations of the site sensor 180, the site sensor 180 may include one or more of the following. The site sensor 180 is a switch. The site sensor 180 is disposable. The site sensor 180 is reusable. The site sensor 180 has a limited life cycle or number of uses. The site sensor 180 is active. The site sensor 180 is passive. The site sensor 180 is electronic. The site sensor 180 is photonic. The site sensor 180 is chemical. The site sensor 180 is mechanical. The site sensor 180 is reactive to any contact, stress, temperature, light, odor, chemical, electrical potential, or any other measurable physical property. The site sensor 180 is reactive to one or more of contact, stress, temperature, light, odor, mechanical, chemical, electrical or electronic property, and any other measurable physical property. The site sensor 180 reacts in the absence of any one of contact, stress, temperature, light, odor, electrical or electronic property, mechanical, chemical, optical or any other physical property of the site sensor 180 being monitored. The site sensor 180 is comprised of various layers of hydrophobic and/or hydrophilic materials. The site sensor 180 is comprised of various layers of transparent, medical-grade, biocompatible materials. One or more of the layers of the site sensor 180 has penetrations, holes, openings, or a path or paths through it or them which would allow liquid underneath to freely flow through the various layer(s). The various penetrations, holes, openings, path or paths of the site sensor 180 are in any number, size, shape, origin, concentration, paucity, permeability, durability or function. The various penetrations, holes, openings, path or paths of the site sensor 180 are differing in number, size, shape, origin, concentration, paucity, permeability, durability or function. The various penetrations, holes, openings, path or paths of the one or more site sensors 180 are differing in number, size, shape, origin, concentration, paucity, permeability, durability or function vary from layer to layer. The membrane layer is reactive to the presence or absence of liquid or vapor and can alter, adjust, moderate, amplify, augment or otherwise vary the size, shape or other feature of the holes, openings, path or paths or any other route through the membrane. The site sensor 180 is a combination of opaque materials. The site sensor 180 contains an area that is perforated, thinned, weakened or otherwise made so as to direct force (a shearing force) along a predetermined path on, along, across, over or otherwise through the site sensor 180 so as to ensure that the patch is separated from itself, or bisected, thus changing the electrical, mechanical, chemical, optical, sonic or any other monitored physical property of the site sensor 180 due to a physical force being applied to it. The site sensor 180 contains the aforementioned perforated, thinned, weakened or force-directing section wherein that section may or may not cross the entirety of the site sensor 180. The perforated, thinned, weakened or force-directing sections of the one or more layers may be different at each layer. The site sensor 180 contains the aforementioned perforated, thinned, weakened or force-directing section wherein that section may not be in a straight line but rather in an angle, circle or other shape as it may be desired. The site sensor 180 contains the aforementioned perforated, thinned, weakened or force-directed section wherein that section is at a corner or at one of the corners or edges of the site sensor 180. The active sensing area of the layers is made of wire, traces, various conductive material, metals, painted traces, liquid conductive applications, sputtered deposition, vapor deposition build up, MEMs production, photolithography, or other electrical connection production method. The site sensor 180 has a conductive phase or array that may or may not dissolve in the presence of a liquid or vapor. The site sensor 180 is in any shape, thickness, or cuvature as may be desirable for application to differing areas of the body. The active sensing area of the differing levels is of differing sizes and/or shapes. The specified area of the site sensor 180, throughout its layers, has a region where there is no active sensing area to allow for penetration through the site sensor 180 itself by a needle or other device or observation or other monitor access. The site sensor 180 has included in it any additional site sensor 180 that is able to determine the actual physical contact with the body being monitored. The site sensor 180 has included in it the ability to sense the degree of actual physical contact with the body being monitored using a applied sensing method such as, but not limited to optical, thermal, and sonic. The site sensor 180 contains wet, dry or both wet and dry components. The site sensor 180 contains any of the known types of "dry jell" products. The site sensor 180 contents and construction may be monolithic or of discrete components. The site sensor 180 is comprised entirely of, or has as components, membranes or layers that are permeable by vapors. The site sensor 180 includes vapor permeable membrane layers where the membrane layers are of differing and/or variable permeability. The site sensor 180 layers are sewn, bonded, connectored, sealed, fused, adhesively attached, glued, melted together or connected by any other method known to those skilled in the art. The perimeter of the site sensor 180 is surrounded by an area of absorbent material. The site sensor 180 includes layers of absorbent materials. The site sensor 180 monitors any physical property that can be measured or gauged. The site sensor 180 is comprised of thermistors, thermal transducers, or thermal detectors to provide output to the analytical circuit. The site sensor 180 uses exothermic or endothermic chemical(s) to enhance the responsiveness of the thermistors, thermal transducers, or thermal detectors. The site sensor 180 uses a hydrophilic product in conjunction with a reed switch or other mechanical switch that would be caused to change states due to pressure from the filling of the hydrophilic materials applying pressure against the switch. The hydrophilic switch may or may not be encased inside of a semi-rigid covering for the purpose of containing and/or directing the pressure towards the switch. The site sensor 180 contains a reed switch or other style of physical switch that is entirely encased in a non-conductive covering which may be of any appropriate material or fabric. The site sensor 180 uses a resonate frequency to determine the status of the site sensor 180. The site sensor 180 uses the electronic determination of the resonate frequency and its stability and range for the purpose of determining the status of the site sensor 180 and is resettable around a new frequency in the case of a partial occlusion of the site sensor 180 or a slight movement of the site sensor 180 area. The site sensor 180 has different chemicals or other discrete sensors applied to the differing layers to aid in the differentiation of what may or may not be coming into contact with the site sensor 180. The site sensor 180 utilizes two or more electrodes and the measurement therebetween to determine contact with the body. The site sensor 180 utilizes a single electrode to determine contact with the body. The site sensor 180 utilizes the separation or spacers between the various layers of the site sensor 180 to control or calibrate the amount of blood or fluid required to activate an alarm condition. The site sensor 180 has a drain hole in one or more areas of the site sensor 180 to allow the occluding blood or fluid to be drained off. The site sensor 180 has one or more holes in a top layer of non-vapor permeable membrane or a limited permeable membrane which would allow the aforementioned holes to be covered with a finger and pressure applied to the site sensor 180 to force blood out of a drain hole in order to reset the site sensor 180. The site sensor 180 has a luer fitting or other appropriate fitting to allow a liquid or gas or vapor to be infused in order purge the internal spaces of the site sensor 180. The site sensor 180 has a suction port to allow the vacuum or suction removal of liquid, blood or occluding vapors. The site sensor 180 contains various chemical-determining sensors which would allow the determination of what liquid is contacting the site sensor 180. The site sensor 180 uses the various optical properties of differing liquids to determine what liquid is contacting the site sensor 180. The site sensor 180 uses a hydrophilic inner layer which has a capacitive or inductive site sensor 180 to determine the presence of liquid. The capacitive or inductive element is external to the sensor 180 itself. The site sensor 180 uses a piezo-electric crystal or device that changes the pressure of a liquid in a hydrophilic pad contained by a rigid or semi-rigid container or package. The site sensor 180 uses electro-active powders that produce an electrical potential or current when wetted.

In one or more further implementations of the site sensor 180, the site sensor 180 may include one or more of the following. The input to the site sensor 180 is an electrical type sensor, a mechanical sensor, a chemical sensor, an optical sensor, or any other type of sensor. The input to the site sensor 180 is a direct current (DC) voltage potential. The input to the site sensor 180 is an alternating current (AC) voltage potential. The input to the site sensor 180 is an amplitude modulated (AM) signal. The input to the site sensor 180 is a frequency modulated (FM) signal. The input to the site sensor 180 is a pulse width modulated signal. The input to the site sensor 180 is a light source (of any wavelength). The input to the site sensor 180 is part of the electromagnetic spectrum. The input to the site sensor 180 is a thermal change. The input to the site sensor 180 is a mechanical force. The input to the site sensor 180 is an electrochemical change. The input to the site sensor 180 is any combination of inputs. The sensor input is sent to a computer file. The sensor input is sent to an electronic storage or media device. The sensor input is displayed on a computer monitor. The sensor input is displayed on a medical device's user interface. The input to the site sensor 180 is different from the output. The site sensor 180 operates in multiple or singular modalities. The site sensor 180 operation may change modalities.

In one or more additional implementations of the site sensor 180, the site sensor 180 may include one or more of the following. The output from the site sensor 180 is electrical, mechanical, chemical, thermal, optical, or any other type of output. The output from the site sensor 180 is a direct current (VDC) voltage potential. The output from the site sensor 180 is an alternating current (VAC) voltage potential. The output from the site sensor 180 is an amplitude modulated (AM) signal. The output from the site sensor 180 is a frequency modulated (FM) signal. The output from the site sensor 180 is a pulse width modulated signal. The output from the site sensor 180 is a light source (of any wavelength). The output from the site sensor 180 is part of the electromagnetic spectrum. The output from the site sensor 180 is a mechanical force. The output from the site sensor 180 is an electrochemical change. The output from the site sensor 180 is any combination of outputs. The site sensor 180 output is different from the input. The sensor input is different from the output. The sensor output is sent to a computer file. The sensor output is sent to an electronic data storage or media device. The sensor output is displayed on a computer monitor. The sensor output is displayed on a medical device's user interface. The sensor output is variable depending on which layers are responding or providing an output or where a variance is detectable. The sensor output is variable or progressive or regressive depending on the amount of liquid detected by the site sensor 180.

Analytical Circuit/Enunciator:

With reference to FIG. 7, an electrical schematic of an embodiment of the analytical circuit 190 is shown. The analytical circuit 190 illustrated is a standard comparator that compares the value of an electrical output signal, in one embodiment, sent through the conductive wires 273 to the site sensor 180 to the value of an input signal received through the conductive wires 273 from the site sensor 180. This allows for the fail-to-safe feature of the present invention because if a difference between the output signal and the input signal is outside a designated range or if there is no return signal as in the case of detachment of the detection section 269 from the site sensor 180, the analytical circuit 190 responds to that change by sending an output signal to the enunciator 200 to be actuated or causing one or more switches to be closed to actuate the enunciator 200. The analytical circuit 180 and the enunciator 200 may be powered by a power supply 302. Although the analytical circuit is show as including a comparator, in alternative embodiments, other analytical circuits may be used to provide the fail-to-safe feature of the present invention. Further, hardware that may perform the functions described herein include, but not by way of limitation, an application specific integrated circuit (ASIC), a set of wired logic circuits, and a hardwired circuit of electrical components, e.g., transistors, capacitors, and resistors. Further, hardware and software may be used to perform the functions described herein. Examples of hardware and software that may perform the functions described herein include, but not by way of limitation, a programmed computer and an application specific computer. The analytical circuit 190 is powered by a power supply.

In one or more implementations of the analytical circuit 190, the analytical circuit 190 may include one or more of the following. The analytical circuit 190 provides electrical isolation in compliance with the nonisolated patient connection requirements of Safe Current Limits for Electromedical Apparatus as required by Applicable Document 2.3. The analytical circuit 190 is part of the sensor 180, 310, 350. The analytical circuit 190 is part of the enunciator 200. The analytical circuit 190 is part of a sensor/enunciator assembly. The analytical circuit 190 may include a reset and/or mute button to reset the analytical circuit 190 in the event of an alarm by the enunciator 200 and/or mute the alarm of the enunciator 200.

In one or more implementations of the enunciator 200, the enunciator 200 may include one or more of the following. The input to the enunciator 200 is the output of an electrical type sensor, a mechanical sensor, a chemical sensor, an optical sensor, or any other type of sensor. The input to the enunciator 200 is a direct current (DC) voltage potential. The input to the enunciator 200 is an alternating current (AC) voltage potential. The input to the enunciator 200 is an amplitude modulated (AM) signal. The input to the enunciator 200 is a frequency modulated (FM) signal. The input to the enunciator 200 is a pulse width modulated signal. The input to the enunciator 200 is a light source (of any wavelength). The input to the enunciator 200 is part of the electromagnetic spectrum. The input to the enunciator 200 is a thermal change. The input to the enunciator 200 is a mechanical force. The input to the enunciator 200 is an electrochemical change. The input to the enunciator 200 is any combination of inputs. The input to the enunciator 200 is different from the output. The enunciator 200 operates in multiple or singular modalities. The enunciator 200 operation may change modalities. The output from the enunciator 200 is electrical, mechanical, chemical, thermal, optical, or any other type of output. The output from the enunciator 200 is a direct current (VDC) voltage potential. The output from the enunciator 200 is an alternating current (VAC) voltage potential. The output from the enunciator 200 is an amplitude modulated (AM) signal. The output from the enunciator 200 is a frequency modulated (FM) signal. The output from the enunciator 200 is a pulse width modulated signal. The output from the enunciator 200 is a light source (of any wavelength). The output from the enunciator 200 is part of the electromagnetic spectrum. The output from the enunciator 200 is a mechanical force. The output from the enunciator 200 is an electrochemical change. The output from the enunciator 200 is any combination of outputs. The sensor output is enunciator 200 is different from the input. The enunciator input is different from the output. The enunciator output is sent to a computer file. The enunciator output is sent to an electronic data storage or media device. The enunciator output is displayed on a computer monitor. The enunciator output is displayed on a medical device's user interface. The enunciator output is variable depending on which layers are responding or providing an output or where a variance is detectable. The enunciator output is variable or progressive or regressive depending on the amount of liquid or rate of change detected by the site sensor 180. The output of the enunciator 200 goes to any electronic data storage device. The independent power supplies for each component may differ from each other. The enunciator 200 output is visual. The enunciator output is audible at any volume or frequency. The enunciator output is vibration. The enunciator output is an electronic signal. The enunciator output is an optical/photonic signal. The enunciator output is any part of the electromagnetic spectrum. The enunciator 200 itself is of any shape or size. The enunciator output is any combination of outputs. The site sensor 180, the analytical circuit 190 and the enunciator 200 are connected to each other with any physical connection device.

In one or more implementations of the power supply 302 of the analytical circuit 190, the power supply 302 may include one or more of the following. The analytical circuit 190 is powered by an external power supply. The analytical circuit 190 is powered by an internal power supply. The analytical circuit 190 is powered by solar energy. The analytical circuit 190 is powered by a combination of external and internal or solar power supplies. The analytical circuit 190 is powered by a combination of differing power supplies which may be internal or external or both. The power supply is a disposable battery. The power supply is a rechargeable battery. The power supply's rechargeable battery is recharged from the medical device it is attached to, such as an infusion pump or dialysis unit. The power supply is a "Cap-Battery" or other power storage device. The power supply is a proprietary or custom battery of varying shapes or voltages or outputs. The power supplies are independent for each component. The power supply has a redundant or a "back-up" arrangement. The power supply is monitored for a low-battery condition. The power supply is monitored for trends in capacity. The power supply is monitored for trends in capacity and indication given as to expected capacity on current cycle and/or remaining cycles before performance is considered to be unacceptable. The state of the power supply is monitored and status is displayed on a user interface such as an indicator light, graphical user interface, monitor (CRT, flat panel, etc.), or any other format as know to those skilled in the art. The power supply is a current storage device.

Method of Use:

With reference to FIGS. 4–7, the system will now be described in use. An electrical signal is sent from the analytical circuit 190 to the active site sensor 180. This signal passes from the first sensing array 240 of the site sensor 180 through the resistor 276 to the second sensing array 250, and back out to the analytical circuit 190. The analytical circuit 190 monitors the return signal. Any change of this returned signal outside of a designated range produces an output, which is sent to the enunciator 200 to actuate an alarm. Monitored conditions that would cause the returned signal to be outside of the designated range include when partial venous needle dislodgment occurs, and when complete venous needle dislodgment occurs.

During partial venous needle dislodgment (not exclusively infiltrating), blood leaking around the fistula needle 150 or otherwise will flow through the base membrane layer 210, contacting the first sensing array 240, and through the second membrane layer 220 thereby coming into contact with the second sensing array 250. Because the sensing arrays 240, 250 are resistively connected and the signal input from the analytical circuit 190 provides a constant value through the system (allowing for a fail-to-safe feature), the change in resistance in the sensing arrays 240, 250 caused by the blood contact alters the signal so that the returned signal to the analytical circuit 190 is outside of the designated range. The analytical circuit 190 responds to this condition by energizing the enunciator 200, causing the alarm.

During complete venous needle dislodgment, the tab 268 that wraps around the bloodline 160 transfers the pulling force causing the dislodgment to the perforation 270 or otherwise weakened area, allowing the detachment section 169 to separate from the rest of the site sensor 180 and cutting the connection between the conductive wires 273 and the sensing arrays 240, 250 so that the electrical circuit is opened. Severing the electrical circuit eliminates the return signal to the analytical circuit 190 so that the difference between the sent signal and returned signal (or lack thereof) is outside of the designated range determined by the analytical circuit 190. The analytical circuit 190 responds to this condition by energizing the enunciator 200, causing the alarm.

Thermal Site Sensor:

With reference to FIG. 9, an alternative embodiment of a site sensor 310 is shown. In this embodiment, one or more sensing arrays 320 include a plurality of thermistors 330 spaced along the sensing array 320 in a space between a base membrane layer and a second membrane layer (and possibly other membrane layers). The thermistors 330 are disposed within an exothermic chemical 340 within the space between the base membrane layer and the second membrane layer (and possibly other membrane layers). The underside of the base membrane layer is adhesively coated near its periphery and has holes that would allow the free passage of vapor, blood, or other fluid therethrough. The exothermic chemical 340 releases its thermal potential when the blood or other fluid contacts it. The resulting thermal change warms the thermistors 330, causing the thermistors 330 to change their resistive values in correlation to the amount of thermal change. This change in resistance is detected by the analytical circuit 190 which produces an alarm. The site sensor 310 includes a detachment section 269 similar to the detachment section 269 described above with respect to FIG. 6.

With reference to FIG. 10, another embodiment of a site sensor 350 is shown. The site sensor 350 may include one or more sensing arrays 360 comprised of one or more optical fibers 370 disposed in a space between a base membrane layer and a second membrane layer (and possibly other membrane layers). Similar to the embodiments shown and described above, the underside of the base membrane layer is adhesively coated near its periphery and has holes that would allow the free passage of vapor, blood or other fluid therethrough. The one or more optical fibers of the sensing array 360 may be connected to a light source. The exterior of the one or more optical fibers may be treated to encourage adhesion of blood or other fluid thereto. Light from the light source passes through the one or more optical fibers between the base membrane layer and the second membrane layer. When blood or other fluid passes through the holes of the base membrane layer and occludes the space between the base membrane layer and the second membrane layer and contacts the one or more optical fibers, the light transmission through the one or more optical fibers is affected. This is detected by the analytical circuit, causing an alarm to be produced. In an alternative embodiment, light may pass through a block or other optical unit that would be occluded in the presence of blood or other liquid, and the analytical circuit may detect this. In another embodiment, a light path may be altered by the physical presence of blood or liquid in the space between layers, altering an optical picture, which is detected by the analytical circuit 190 and sets off the alarm.

It will be readily apparent to those skilled in the art that still further changes and modifications in the actual concepts described herein can readily be made without departing from the spirit and scope of the invention as defined by the following claims.

What is claimed is:

1. A hemodialysis site sensor attachable to at least one of a blood line and a fistula needle for alerting medical personnel of the leakage of blood from an access site where the fistula needle enters into a patient's body and dislodgment of the fistula needle from the access site, the hemodialysis site sensor comprising:
    a base membrane layer made of a medical-grade, biocompatible material and including an upper side, a lower side adherable to skin of the patient, and one or more holes disposed therein to allow the passage of blood and vapor therethrough;
    a second membrane layer including an upper side, a lower side, and one or more holes disposed therein to allow the passage of blood and vapor therethrough;
    a third membrane layer including an upper side and a lower side;
    an electrical connection adapted to be electrically coupled to an analytical circuit and including
        a first sensing array disposed between the upper side of the base membrane layer and the lower side of the second membrane layer,
        a second sensing array disposed between the upper side of the second membrane layer and the lower side of the third membrane layer, and resistively connected to the first sensing array;
    a disconnection mechanism attachable to at least one of the blood line and the fistula needle and severing the electrical connection upon dislodgment of the fistula needle from the access site;
    wherein an electrical signal sent through the electrical connection changes when blood contacts at least one of the sensing arrays or the electrical connection is severed by the disconnection mechanism, causing the analytical circuit to actuate an alarm notifying medical personnel of partial or total dislodgment of the fistula needle from the access site.

2. The hemodialysis site sensor of claim 1, wherein the disconnection mechanism includes an adhesive tab attachable to at least one of the blood line and the fistula needle, and a perforation along the membrane layers so that upon dislodgment of the fistula needle, the dislodgment mechanism separates from the site sensor along the perforation, causing the electrical connection to be severed.

3. The hemodialysis site sensor of claim 1, wherein the electrical connection include a conductive wire that wraps around a patient's limb where the access site is.

4. A method of alerting medical personnel of partial and total dislodgment of a fistula needle from an access site where the fistula needle enters into a patient's body during hemodialysis, comprising:
    providing a site sensor including a base membrane layer made of a medical-grade, biocompatible material and including a lower side adherable to skin of the patient at the access site, and one or more holes disposed therein to allow the passage of blood and vapor therethrough, a top membrane layer, an electrical connection including one or more resistively connected sensing arrays disposed between the base membrane layer and the top membrane layer, and a disconnection mechanism attachable to at least one of the blood line and the fistula needle and severing the electrical connection upon dislodgment of the fistula needle from the access site;
    providing an analytical circuit in electrical communication with the electrical connection;
    sending a signal from the analytical circuit to the site sensor and receiving the signal from the site sensor with the analytical circuit, the signal traveling through the one or more resistively connected sensing arrays of the electrical connection;
    partially dislodging the fistula needle from the access site causing blood to contact the one or more resistively connected sensing arrays and the signal sent from the analytical circuit to change;
    completely dislodging the fistula needle from the access site causing the disconnection mechanism to sever the electrical connection and the signal sent from the analytical circuit to change;
    determining with the analytical circuit whether the signal changed outside of a predetermined range;
    actuating an alarm with the analytical circuit if the signal changed outside of a predetermined range.

5. The method of claim 4, wherein the disconnection mechanism includes an adhesive tab attachable to at least one of the blood line and the fistula needle, and a perforation along the membrane layers, and severing the electrical connection with the disconnection mechanism includes severing the electrical connection by at least one of the blood line and the fistula needle pulling on the adhesive tab and separating the dislodgment mechanism from the site sensor along the perforation, causing the electrical connection to be severed.

6. The method of claim 5, wherein the site sensor further includes a first membrane layer including one or more holes disposed therein to allow the passage of blood and vapor therethrough, and the one or more resistively connected sensing arrays include a first sensing array disposed between the base membrane layer and the first membrane layer, and a second sensing array disposed between the first membrane layer and the top membrane layer.

7. The method of claim 5, further including resetting the site sensor in the event of false alarm.

8. A method of alerting medical personnel of a problem during hemodialysis, comprising:

providing an active, fail-to-safe site sensor for a fistula needle at an access site during hemodialysis, wherein the active, fail-to-safe sensor includes a base membrane layer made of a medical-grade, biocompatible material and including a lower side adherable to skin of the patient, and one or more holes disposed therein to allow the passage of blood and vapor therethrough, a top membrane layer, an electrical connection including one or more resistively connected sensing arrays disposed between the base membrane layer and the top membrane layer, and an analytical circuit in electrical communication with the one or more resistively connected sensing arrays of the electrical connection and sending an electrical signal therethrough, and automatically alerting medical personnel of a problem during hemodialysis using the active, fail-to-safe site sensor when the difference between the electrical signal sent by the analytical circuit and the electrical signal received by the analytical circuit is beyond a predetermined range, and automatically alerting medical personnel of a problem during hemodialysis using the active, fail-to-safe site sensor during at least the following: failing of the active, fail-to-safe site sensor, insufficient powering to the active, fail-to-safe site sensor, partial fistula needle dislodging from the access site; and complete needle dislodging from the access site.

9. The method of claim 8, wherein the active, fail-to-safe site sensor includes an active electric circuit and a disconnection mechanism attached to at least one of a blood line and the fistula needle that opens the active electric circuit of the active, fail-to-safe site sensor during complete needle dislodgment, and complete needle dislodging from the access site includes causing the disconnection mechanism to open the active electric circuit of the active, fail-to-safe site sensor.

10. The method of claim 8, wherein the active, fail-to-safe site sensor further includes a first membrane layer including one or more holes disposed therein to allow the passage of blood and vapor therethrough, and the one or more resistively connected sensing arrays include a first sensing array disposed between the base membrane layer and the first membrane layer, and a second sensing array disposed between the first membrane layer and the top membrane layer.

11. The method of claim 8, further including resetting the site sensor in the event of false alarm.

* * * * *